(12) United States Patent
Miyachi et al.

(10) Patent No.: US 9,724,291 B2
(45) Date of Patent: Aug. 8, 2017

(54) EXTERNAL SKIN PREPARATION

(71) Applicant: NOEVIR CO., LTD., Hyogo (JP)

(72) Inventors: Nobuyuki Miyachi, Shiga (JP); Kenta Shingaki, Shiga (JP); Sachi Kawaguchiya, Shiga (JP)

(73) Assignee: NOEVIR CO., LTD., Hyogo (JP)

( * ) Notice: Subject to any disclaimer, the term of this patent is extended or adjusted under 35 U.S.C. 154(b) by 161 days.

(21) Appl. No.: 14/745,714

(22) Filed: Jun. 22, 2015

(65) Prior Publication Data

US 2015/0366785 A1   Dec. 24, 2015

(30) Foreign Application Priority Data

Jun. 24, 2014   (JP) ................. 2014-128847

(51) Int. Cl.
*A61K 36/00* (2006.01)
*A61K 8/97* (2017.01)
*A61Q 19/08* (2006.01)
*A61Q 19/00* (2006.01)

(52) U.S. Cl.
CPC ........... *A61K 8/97* (2013.01); *A61Q 19/00* (2013.01); *A61Q 19/08* (2013.01); *A61K 2800/5922* (2013.01)

(58) Field of Classification Search
None
See application file for complete search history.

(56) References Cited

U.S. PATENT DOCUMENTS

| 2013/0202541 A1 | 8/2013 | Dahlgren et al. |
| 2014/0308222 A1 | 10/2014 | Dahlgren et al. |

FOREIGN PATENT DOCUMENTS

| CH | 696135 A5 * | 1/2007 | ............... A61K 8/64 |
| JP | 2001-288032 | 10/2001 | |
| JP | 2004-010526 | 1/2004 | |
| JP | 2004-107268 | 4/2004 | |
| JP | 2005-126353 | 5/2005 | |
| JP | 2006-193495 | 7/2006 | |
| JP | 2006193495 A * | 7/2006 | |
| JP | 2009-196980 | 9/2009 | |
| JP | 2013-518101 | 5/2013 | |

OTHER PUBLICATIONS

Able C&C Missha Signature Dramatic Whitening Pact SPF 50+ PA+++, Mintel GNPD [online], Mintel Group Ltd., pp. 627-633, record ID 1816405, Jun. 2012.
Dr. Morita Purifying Balancing Mask, Mintel GNPD [online], Mintel Group Ltd., pp. 254-257, Record ID 2224844, Nov. 2013.
Ulrich Justrich Just Body Lotion, Mintel GNPD [online], Mintel Group Ltd., pp. 1188-1190, Record ID 1194459, Oct. 2009.
Naruko Lupin Anti-Wrinkle Firming Eye Cream Ex, Mintel GNPD [online], Mintel Group Ltd., pp. 142-146, Record ID 2277947, Jan. 2014.
Naruko Taiwan Magnolia Brightening and Firming Night Gelly Ex, Mintel GNPD [online], Mintel Group Ltd., pp. 262-267, Record ID 2215481, Oct. 2013.
DM Alverde Naturkosmetik Kleine Elfe Baby Sun Cream SPF30, Mintel GNPD [online], Mintel Group Ltd., pp. 899-901, Record ID 1599663, Jul. 2011.
Naruko Taiwan Magnolia Firming Smooth Finish Cream Make Up SPF50, Mintel GNPD [online], Mintel Group Ltd., pp. 41-45, Record ID 2352477, Mar. 2014.
Office Action for Japanese Patent Application No. 2014-128847, mailed Dec. 2, 2014.
Office Action for Japanese Patent Application No. 2014-128847, mailed Mar. 17, 2015.

* cited by examiner

*Primary Examiner* — Qiuwen Mi
(74) *Attorney, Agent, or Firm* — Greenblum & Bernstein, P.L.C.

(57) ABSTRACT

An external skin preparation containing an edelweiss extract, and one or more extracts selected from the group consisting of extracts of plants belonging to the genus *Artemisia*, pipsissewa extract, olive extract, jojoba extract, carambola extract, clove extract, chamomile extract, carrot extract, daisy extract, peach kernel extract, marsh mallow extract, cinnamon bark extract, told extract, marigold extract, parsley extract, coltsfoot extract, creeping saxifrage extract and European elderberry extract.

12 Claims, 7 Drawing Sheets

[FIG. 1]
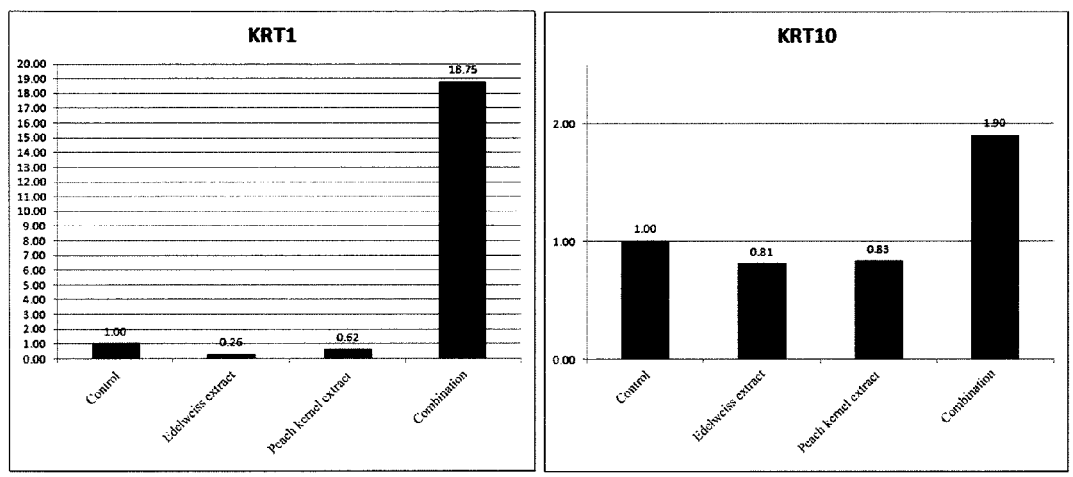
[FIG. 2]
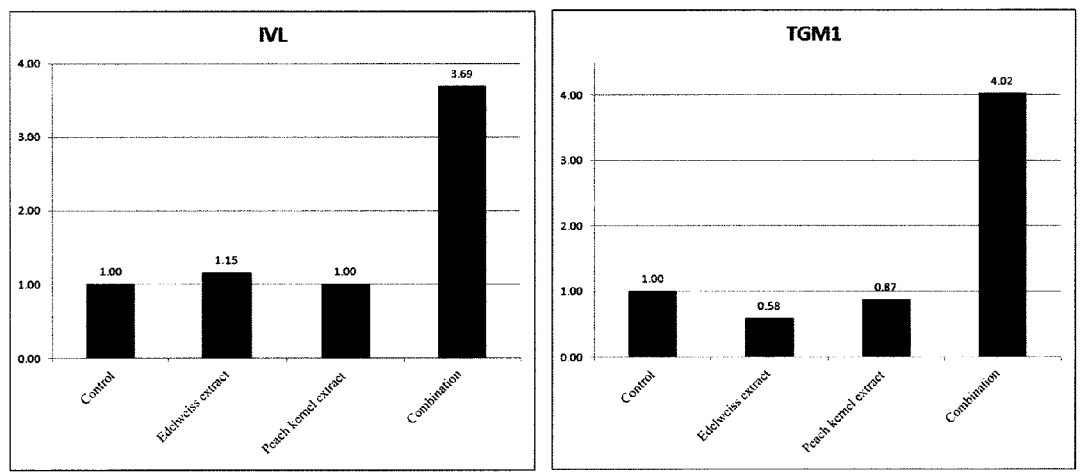

[FIG. 3]
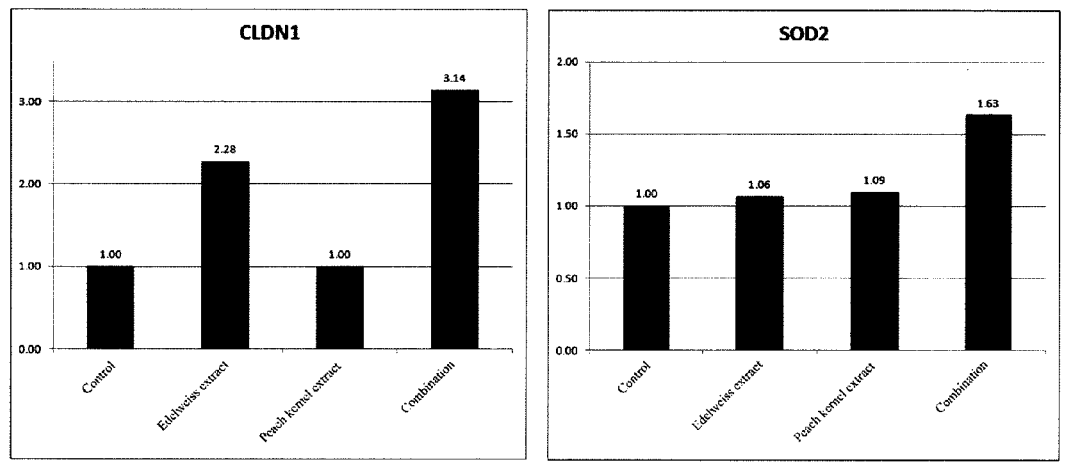
[FIG. 4]
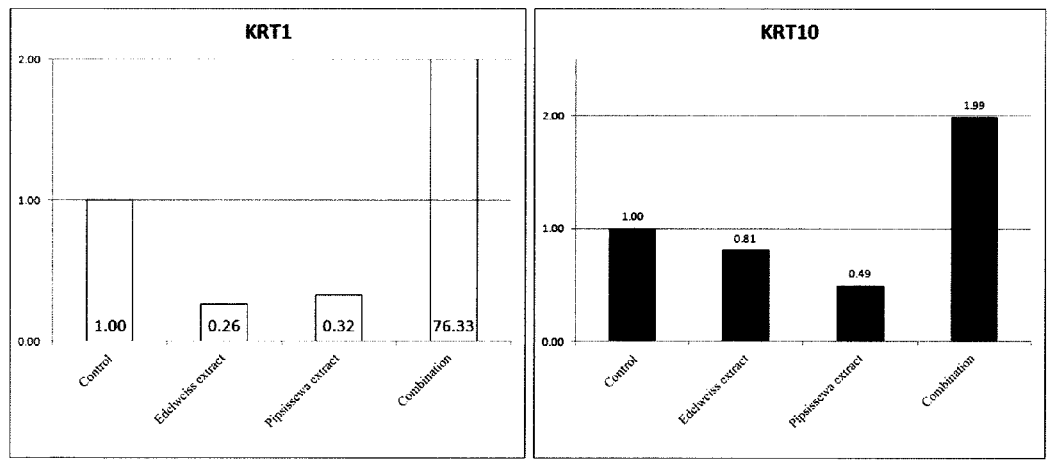

[FIG. 5]
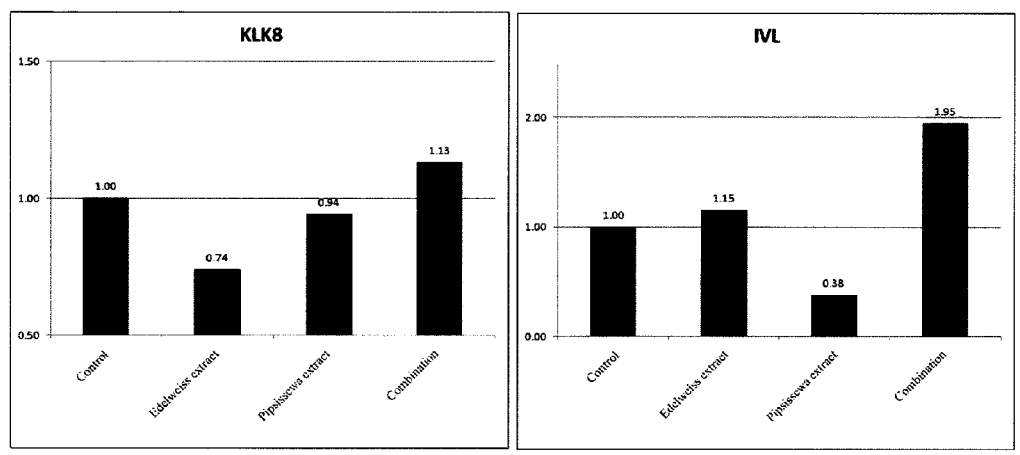
[FIG. 6]
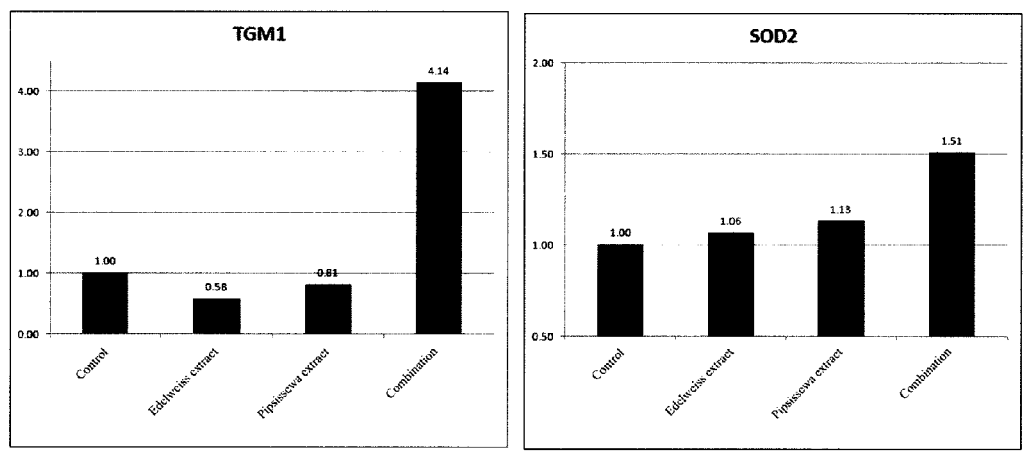

[FIG. 7]
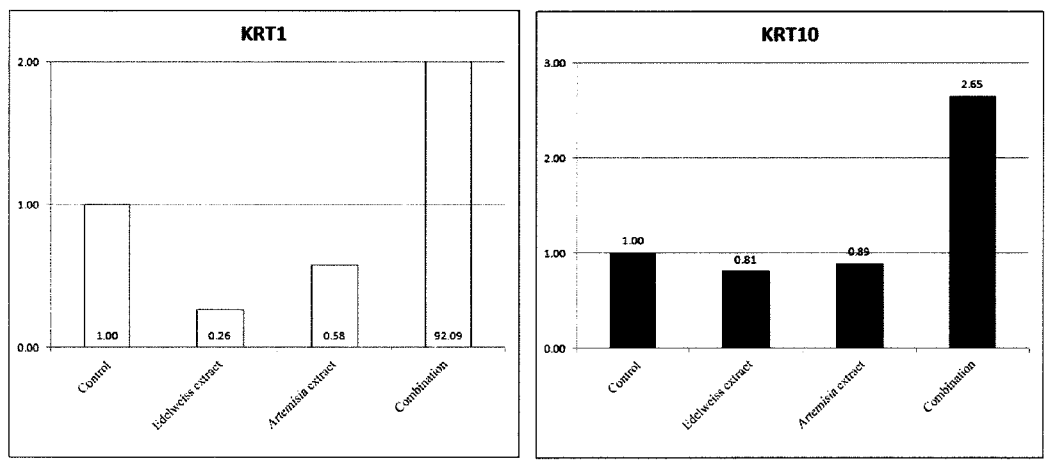
[FIG. 8]
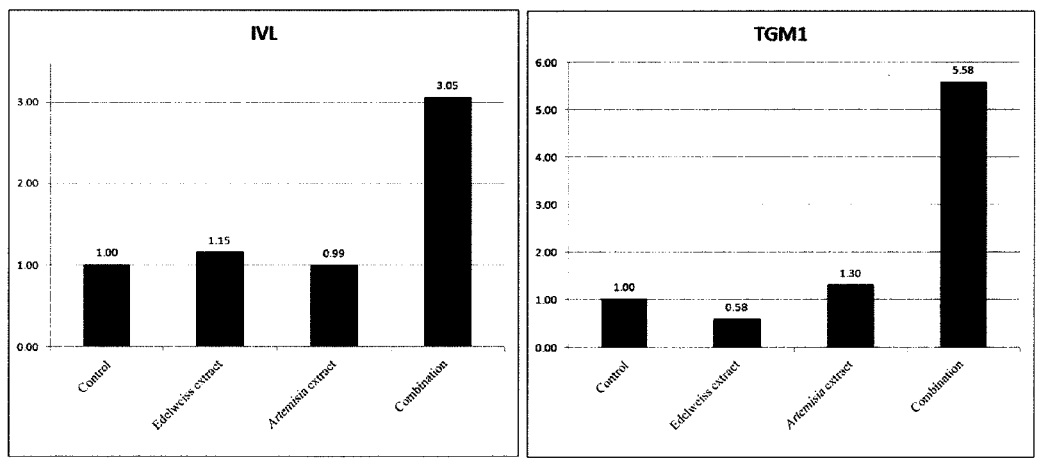

[FIG. 9]
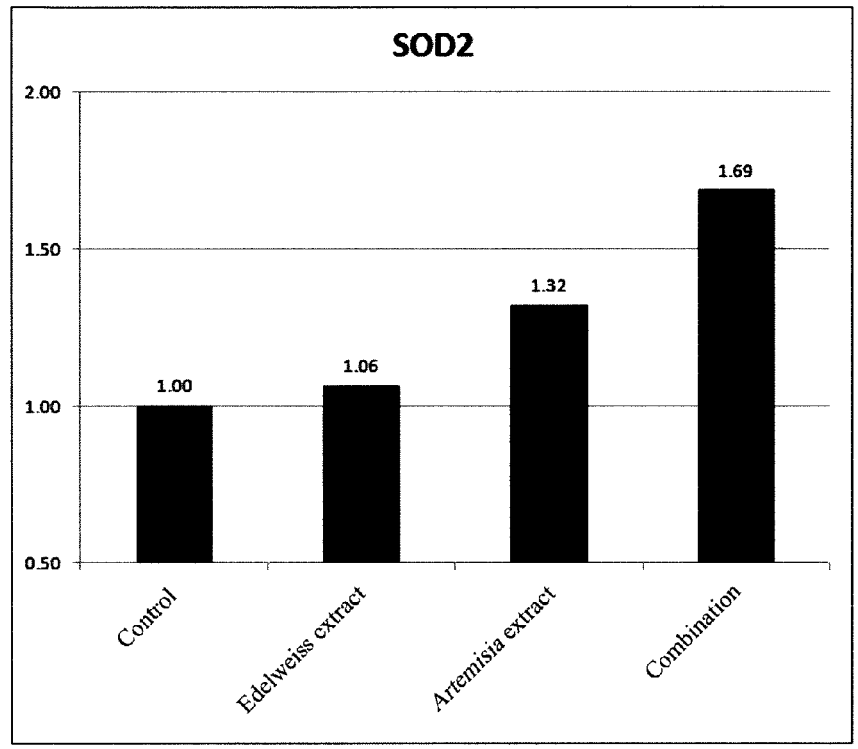
[FIG. 10]
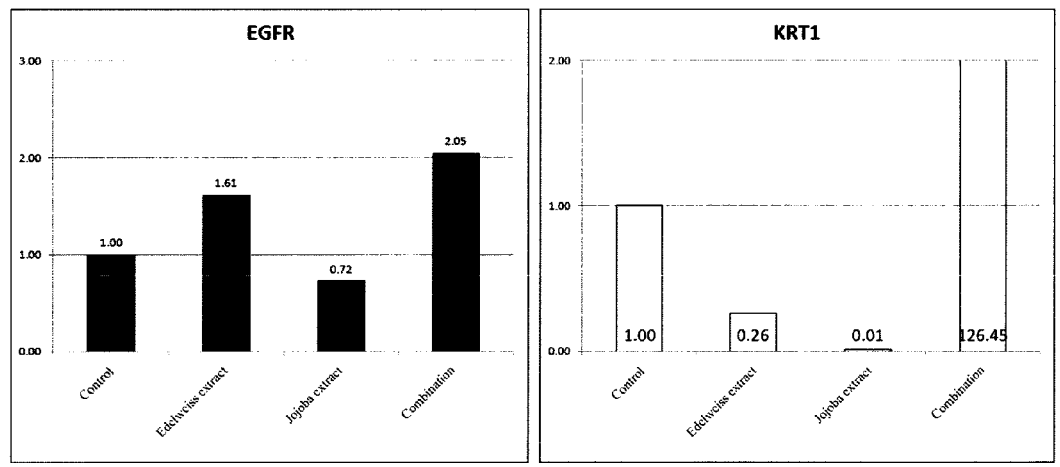

[FIG. 11]
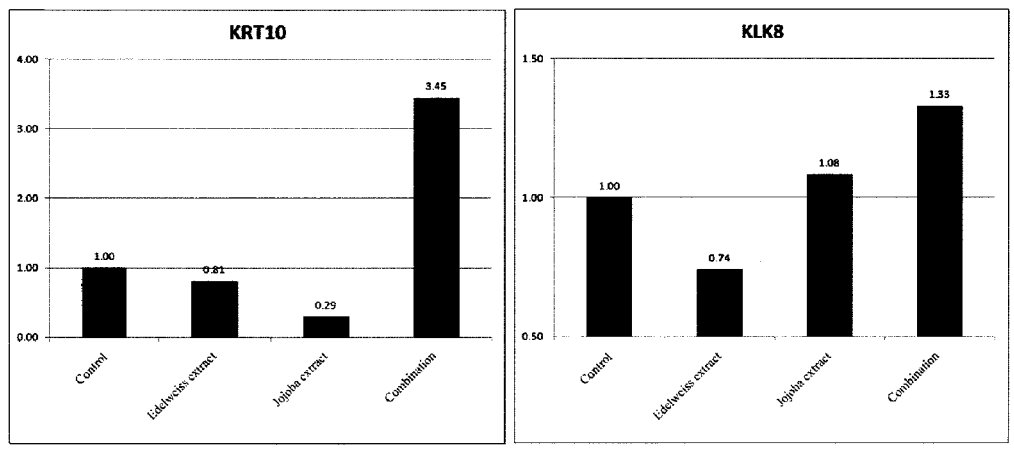
[FIG. 12]
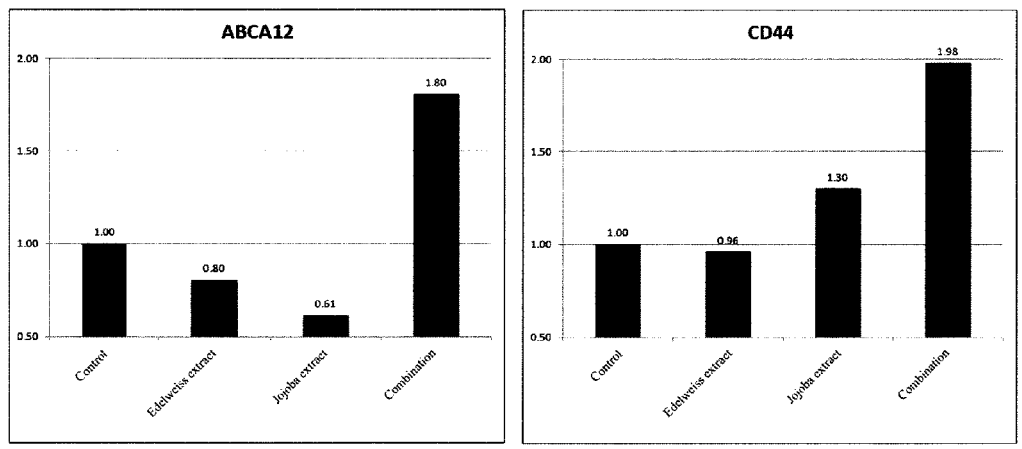

[FIG. 13]
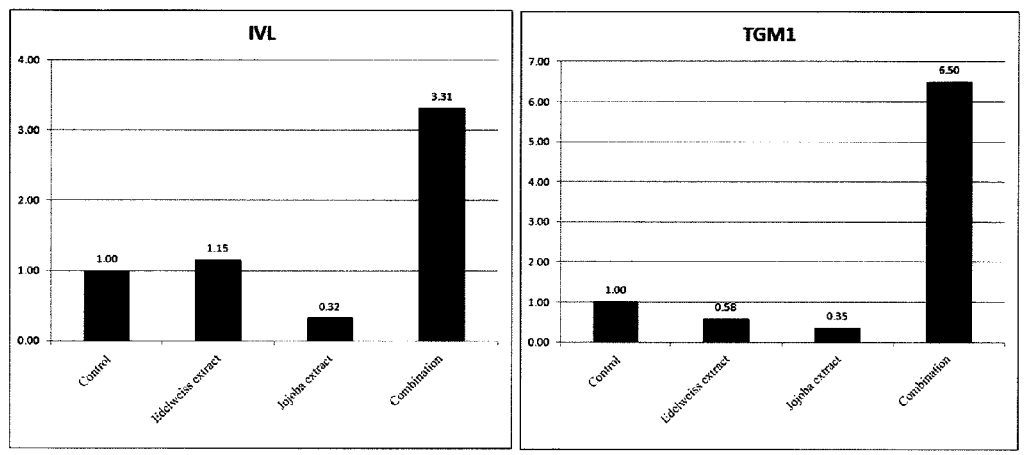
[FIG. 14]
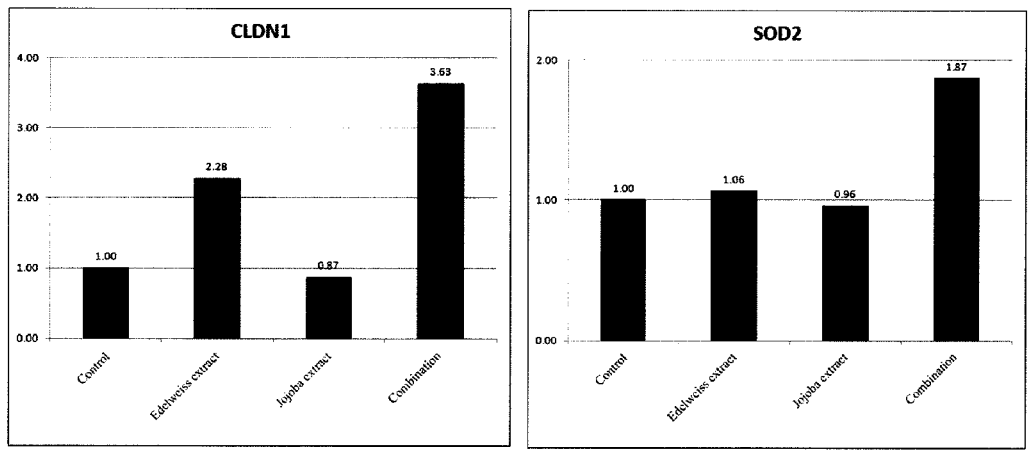

EXTERNAL SKIN PREPARATION

CROSS REFERENCE TO RELATED APPLICATIONS

This Application is based upon and claims the benefit of priority from prior Japanese Patent Application No. 2014-128847 filed on Jun. 24, 2014; the entire contents of which are incorporated by reference herein.

SEQUENCE LISTING

The instant application contains a Sequence Listing which has been submitted electronically in ASCII format and is hereby incorporated by reference in its entirety. Said ASCII copy, created on Jul. 22, 2015, is named P48032_SL.txt and is 5,259 bytes in size.

BACKGROUND OF INVENTION

Technical Field

Embodiments of the present invention relate to external skin preparations prepared using a combination of an edelweiss extract and a specific plant extract.

Related Art

Edelweiss (*Leontopodium alpinum*) is an alpine plant belonging to the genus *Leontopodium* of the Asteraceae, and the addition of an extract of edelweiss to an external skin preparation is already known (see JP 2001-288032 A).

Further, numerous investigations have been conducted into the inclusion of combinations of plant extracts in external skin preparations. However, simply combining plant extracts does not necessarily result in a synergistic improvement in effects, and many combinations yield either an additive improvement in effects, or a mutual cancellation of effects. In this manner, the effects achieved for any particular combination are impossible to predict, and the demand for plant extract combinations which yield superior effects with minimal amounts is extremely high.

SUMMARY OF INVENTION

An object of embodiments of the present invention is to provide external skin preparations which, by combining an edelweiss extract and a specific plant extract, are able to exhibit a superior moisturizing effect and a superior anti-aging effect.

One embodiment of the present invention provides an external skin preparation comprising an edelweiss extract, and one or more extracts selected from the group consisting of extracts of plants belonging to the genus *Artemisia*, pipsissewa (*Chimaphila umbellata*) extract, olive (*Olea europaea*) extract, jojoba (*Simmondsia chinensis*) extract, carambola (*Averrhoa carambola*) extract, clove (*Eugenia caryophyllus, Syzygium aromaticum*) extract, chamomile (*Chamomilla recutita*) extract, carrot (*Daucus carota* var. *sativa*) extract, daisy (*Bellis perennis*) extract, peach (*Prunus persica*) kernel extract, marsh mallow (*Althea officinalis*) extract, cinnamon (*Cinnamomum cassia*) bark extract, toki (*Angelica acutiloba Kitagawa* or *Angelica acutiloba Kitagawa* var. *sugiyamae Hikino* (*Umbelliferae*)) extract, marigold (*Calendula officinalis*) extract, parsley (*Carum petroselinum*) extract, coltsfoot (*Tussilago farfara*) extract, creeping saxifrage (*Saxifraga sarmentosa*) extract and European elderberry (*Sambucus nigra*) extract.

Another embodiment provides an external skin preparation comprising an edelweiss extract, and one or more extracts selected from the group consisting of extracts of plants belonging to the genus *Artemisia*, pipsissewa extract, olive leaf extract, jojoba leaf extract, carambola extract, clove extract, carrot extract, daisy extract, peach kernel extract, marsh mallow extract, cinnamon bark extract, marigold extract, parsley extract, coltsfoot extract and creeping saxifrage extract.

Yet another embodiment provides an external skin preparation comprising an edelweiss extract, and one or more extracts selected from the group consisting of pipsissewa extract, olive leaf extract, jojoba leaf extract, carambola extract, peach kernel extract and parsley extract.

As a result of including a combination of an edelweiss extract and a specific plant extract, the external skin preparations according to the above embodiments exhibit a superior moisturizing effect and a superior anti-aging effect.

BRIEF DESCRIPTION OF DRAWINGS

FIG. 1 is a diagram illustrating a synergistic improvement in the expression of genes related to improved skin turnover by using a combination of an edelweiss extract and a peach kernel extract.

FIG. 2 is a diagram illustrating a synergistic improvement in the expression of genes related to improved skin barrier function by using a combination of an edelweiss extract and a peach kernel extract.

FIG. 3 is a diagram illustrating a synergistic improvement in the expression of genes related to improved skin barrier function and antioxidant function by using a combination of an edelweiss extract and a peach kernel extract.

FIG. 4 is a diagram illustrating a synergistic improvement in the expression of genes related to improved skin turnover by using a combination of an edelweiss extract and a pipsissewa extract.

FIG. 5 is a diagram illustrating a synergistic improvement in the expression of genes related to improved skin turnover and improved skin barrier function by using a combination of an edelweiss extract and a pipsissewa extract.

FIG. 6 is a diagram illustrating a synergistic improvement in the expression of genes related to improved skin barrier function and antioxidant function by using a combination of an edelweiss extract and a pipsissewa extract.

FIG. 7 is a diagram illustrating a synergistic improvement in the expression of genes related to improved skin turnover by using a combination of an edelweiss extract and an *Artemisia* (*Artemisia montana*) extract.

FIG. 8 is a diagram illustrating a synergistic improvement in the expression of genes related to improved skin barrier function by using a combination of an edelweiss extract and an *Artemisia* (*Artemisia montana*) extract.

FIG. 9 is a diagram illustrating a synergistic improvement in the expression of a gene related to antioxidant function by using a combination of an edelweiss extract and an *Artemisia* (*Artemisia montana*) extract.

FIG. 10 is a diagram illustrating a synergistic improvement in the expression of genes related to improved skin turnover by using a combination of an edelweiss extract and a jojoba extract.

FIG. 11 is a diagram illustrating a synergistic improvement in the expression of genes related to improved skin turnover by using a combination of an edelweiss extract and a jojoba extract.

FIG. 12 is a diagram illustrating a synergistic improvement in the expression of genes related to improved skin barrier function by using a combination of an edelweiss extract and a jojoba extract.

FIG. 13 is a diagram illustrating a synergistic improvement in the expression of genes related to improved skin barrier function by using a combination of an edelweiss extract and a jojoba extract.

FIG. 14 is a diagram illustrating a synergistic improvement in the expression of genes related to improved skin barrier function and antioxidant function by using a combination of an edelweiss extract and a jojoba extract.

DESCRIPTION OF EMBODIMENTS

Embodiments for implementing the present invention are described below.

The edelweiss (*Leontopodium alpinum*) added to the external skin preparations of the embodiments of the present invention is an alpine plant belonging to the genus *Leontopodium* of the Asteraceae, and cultivated plants are used. There are no particular limitations on the portion of the plant that is extracted, provided the extract can be blended into the external skin preparation, but the use of one or more portions selected from among the entire plant, the stalks, the flowers, the leaves and the roots is preferable, and the use of the entire plant except the roots is particularly preferable.

The method used for preparing the aforementioned edelweiss extract is described below, but the present invention is not limited to the following extraction solvents and extraction method. Extraction solvents that can be used favorably include one solvent, or a mixture of two or more solvents, selected from among polar solvents including water, alcohols such as ethanol, methanol, isopropanol, isobutanol, n-hexanol, methyl amyl alcohol, 2-ethylbutanol and n-octyl alcohol, polyhydric alcohols or derivatives thereof such as glycerol, ethylene glycol, ethylene glycol monomethyl ether, ethylene glycol monoethyl ether, propylene glycol, propylene glycol monomethyl ether, propylene glycol monoethyl ether, triethylene glycol, 1,3-butylene glycol, hexylene glycol and pentylene glycol, ketones such as acetone, methyl ethyl ketone, methyl isobutyl ketone and methyl n-propyl ketone, esters such as ethyl acetate and isopropyl acetate, and ethers such as ethyl ether, isopropyl ether and n-butyl ether. A phosphate buffered saline solution can also be used. Alternatively, one solvent, or a mixture of two or more solvents, selected from among low-polarity or non-polar solvents including hydrocarbons such as petroleum ether, n-hexane, n-pentane, n-butane, n-octane, cyclohexane and squalane, as well as carbon tetrachloride, chloroform, dichloromethane, trichloroethylene, benzene, and toluene and the like can also be used favorably. Moreover, one or more supercritical fluids or subcritical fluids such as water, carbon dioxide, ethylene, propylene, ethanol, methanol and ammonia may also be used.

Typical examples of the extraction method include methods of performing extraction by solvent immersion, under normal pressure, pressurized or reduced pressure conditions, and at room temperature or under cooling or heating, methods of performing extraction using a distillation method such as steam distillation, and a pressing method of obtaining an extract by pressing the edelweiss. These methods may be used individually, or the extraction may be performed using a combination two or more methods.

The edelweiss extract obtained in this manner may be used as is, or may be subjected to one or more purification operations such as deodorization, decolorization or concentration, or subjected to fractionation using column chromatography or the like, provided these operations do not impair the effects of the extract. The extract, purified product thereof, or fraction thereof, may be converted to a dry solid by removal of the solvent, or may be used in the form of a solution or emulsion in a solvent such as an alcohol.

In the present embodiment, the use of an ethanol aqueous solution extract of edelweiss is preferable.

The amount of the edelweiss extract added to the external skin preparation varies depending on the presence of solvent in the extract and the extract formulation, but is typically about 0.0001 to 1% by mass. The amount is more preferably about 0.001 to 1% by mass, and still more preferably from 0.01 to 1% by mass.

The external skin preparation of the present embodiment includes a combination of the edelweiss extract (1) described above and another specific plant extract (2). The various plant extracts that may be added as this extract (2) are described below.

The extract of a plant belonging to the genus *Artemisia* is not particularly limited, provided the extract can be blended into the external skin preparation. Specific examples of plants belonging to the genus *Artemisia* include mugwort (*Artemisia vulgaris*), capillary wormwood (*Artemisia capillaris*), absinth wormwood (*Artemisia absinthium*), *Artemisia mongolica*, *Artemisia montana*, and *Tanacetum vulgare*, but in terms of the effects of the present embodiment, the use of *Artemisia montana* is preferable. The portion of the plant that is extracted is preferably one or more portions selected from among the leaves, the stalks, the flowers, the entire plant, and the entire above-ground portion of the plant, and the leaves are particularly preferable. Examples of the extraction solvent and the extraction method are the same as those described above for the extraction of edelweiss. One preferred extraction solvent is an ethanol aqueous solution.

The extract of pipsissewa (*Chimaphila umbellata*) is not particularly limited, provided the extract can be blended into the external skin preparation. The portion of the pipsissewa that is extracted is preferably one or more portions selected from among the entire plant, the stalks, the flowers and the leaves, and extraction of the entire plant is particularly preferable. Examples of the extraction solvent and the extraction method are the same as those described above for the extraction of edelweiss. One preferred extraction solvent is an ethanol aqueous solution.

The extract of olive (*Olea europaea*) is not particularly limited, provided the extract can be blended into the external skin preparation. The portion of the olive that is extracted is preferably one or more portions selected from among the leaves, the flowers and the fruit, and extraction of the leaves is particularly preferable. Examples of the extraction solvent and the extraction method are the same as those described above for the extraction of edelweiss. One preferred extraction solvent is an ethanol aqueous solution.

The extract of jojoba (*Simmondsia chinensis*) is not particularly limited, provided the extract can be blended into the external skin preparation. The portion of the jojoba that is extracted is preferably one or more portions selected from among the leaves, the flowers and the fruit, and extraction of the leaves is particularly preferable. Examples of the extraction solvent and the extraction method are the same as those described above for the extraction of edelweiss. One preferred extraction solvent is an ethanol aqueous solution.

The extract of carambola (*Averrhoa carambola*) is not particularly limited, provided the extract can be blended into the external skin preparation. The portion of the carambola that is extracted is preferably one or more portions selected from among the leaves, the flowers and the fruit, and extraction of the leaves is particularly preferable. Examples of the extraction solvent and the extraction method are the same as those described above for the extraction of edelweiss. One preferred extraction solvent is an ethanol aqueous solution.

The extract of clove (*Eugenia caryophyllus, Syzygium aromaticum*) is not particularly limited, provided the extract can be blended into the external skin preparation. The portion extracted is preferably the buds of the clove plant. Examples of the extraction solvent and the extraction method are the same as those described above for the extraction of edelweiss. One preferred extraction solvent is an ethanol aqueous solution.

The extract of chamomile (*Chamomilla recutita*) is not particularly limited, provided the extract can be blended into the external skin preparation. The portion of the chamomile that is extracted is preferably one or more portions selected from among the leaves, the stalks and the flowers, and extraction of the leaves and/or the flowers is particularly preferable. Examples of the extraction solvent and the extraction method are the same as those described above for the extraction of edelweiss. One preferred extraction solvent is an ethanol aqueous solution.

The extract of carrot (*Daucus carota* var. *sativa*) is not particularly limited, provided the extract can be blended into the external skin preparation. The portion extracted is preferably the root of the carrot. Examples of the extraction solvent and the extraction method are the same as those described above for the extraction of edelweiss. Preferred extraction solvents include one or more solvents selected from among 1,3-butylene glycol aqueous solutions, 1,2-pentanediol aqueous solutions, propylene glycol aqueous solutions, ethanol aqueous solutions and water, and the use of a 1,3-butylene glycol aqueous solution is the most desirable.

The extract of daisy (*Bellis perennis*) is not particularly limited, provided the extract can be blended into the external skin preparation. The portion of the daisy that is extracted is preferably one or more portions selected from among the entire plant, the leaves, the stalks, the flowers and the seeds, and extraction of the flowers is particularly preferable. Examples of the extraction solvent and the extraction method are the same as those described above for the extraction of edelweiss. Preferred extraction solvents include one or more solvents selected from among water, ethanol aqueous solutions, 1,3-butylene glycol aqueous solutions, 1,2-pentanediol aqueous solutions and propylene glycol aqueous solutions, and the use of a water extract is the most desirable.

Peach kernel refers to the seed of *Prunus persica*, and the peach kernel extract is not particularly limited, provided the extract can be blended into the external skin preparation. Examples of the extraction solvent and the extraction method are the same as those described above for the extraction of edelweiss. Preferred extraction solvents include one or more solvents selected from among 1,3-butylene glycol aqueous solutions, 1,2-pentanediol aqueous solutions, propylene glycol aqueous solutions, ethanol aqueous solutions and water, and the use of an ethanol aqueous solution is the most desirable.

The extract of marsh mallow (*Althea officinalis*) is not particularly limited, provided the extract can be blended into the external skin preparation. The portion of the marsh mallow that is extracted is not particularly limited, and one or more portions selected from among the entire plant, the leaves, the stalks, the flowers, the fruit and the roots may be used. Use of the roots or leaves is preferable, and the leaves are particularly desirable. Examples of the extraction solvent and the extraction method are the same as those described above for the extraction of edelweiss. Preferred extraction solvents include one or more solvents selected from among water, ethanol aqueous solutions, 1,3-butylene glycol aqueous solutions, 1,2-pentanediol aqueous solutions and propylene glycol aqueous solutions, and the use of an ethanol aqueous solution extract is the most desirable.

Cinnamon bark refers to the bark of *Cinnamomum cassia* and other species of the same genus, and the cinnamon bark extract is not particularly limited, provided the extract can be blended into the external skin preparation. Examples of the extraction solvent and the extraction method are the same as those described above for the extraction of edelweiss. Preferred extraction solvents include one or more solvents selected from among 1,3-butylene glycol aqueous solutions, 1,2-pentanediol aqueous solutions, propylene glycol aqueous solutions, ethanol aqueous solutions and water, and the use of an ethanol aqueous solution is the most desirable.

The extract of told (*Angelica acutiloba Kitagawa* or *Angelica acutiloba Kitagawa* var. *sugiyamae Hikino* (*Umbelliferae*)) is not particularly limited, provided the extract can be blended into the external skin preparation. The portion of the told that is extracted is not particularly limited, and one or more portions selected from among the entire plant, the leaves, the stalks, the flowers, the fruit and the roots may be used. Extraction of the roots is particularly desirable. Examples of the extraction solvent and the extraction method are the same as those described above for the extraction of edelweiss. Preferred extraction solvents include one or more solvents selected from among 1,3-butylene glycol aqueous solutions, 1,2-pentanediol aqueous solutions, propylene glycol aqueous solutions, ethanol aqueous solutions and water, and the use of an ethanol aqueous solution is the most desirable.

The extract of marigold (*Calendula officinalis*) is not particularly limited, provided the extract can be blended into the external skin preparation. The portion of the marigold that is extracted is not particularly limited, and one or more portions selected from among the entire plant, the leaves, the stalks, the flowers, the fruit and the roots may be used. Use of the flowers is preferable. Examples of the extraction solvent and the extraction method are the same as those described above for the extraction of edelweiss. Preferred extraction solvents include one or more solvents selected from among 1,3-butylene glycol aqueous solutions, 1,2-pentanediol aqueous solutions, propylene glycol aqueous solutions, ethanol aqueous solutions and water, and the use of a 1,3-butylene glycol aqueous solution is the most desirable.

The extract of parsley (*Carum petroselinum*) is not particularly limited, provided the extract can be blended into the external skin preparation. The portion of the parsley that is extracted is not particularly limited, and one or more portions selected from among the entire plant, the leaves, the stalks, the flowers, the seeds and the roots may be used. Use of one or more portions selected from among the leaves, the stalks and the roots is preferable, and use of the leaves and stalks is particularly desirable. Examples of the extraction solvent and the extraction method are the same as those described above for the extraction of edelweiss. Preferred extraction solvents include one or more solvents selected from among 1,3-butylene glycol aqueous solutions, 1,2-pentanediol aqueous solutions, propylene glycol aqueous solutions, ethanol aqueous solutions and water, and the use of water is the most desirable.

The extract of coltsfoot (*Tussilago farfara*) is not particularly limited, provided the extract can be blended into the external skin preparation. The portion of the coltsfoot that is extracted is not particularly limited, and one or more portions selected from among the entire plant, the leaves, the stalks, the flowers, the seeds and the roots may be used. Use of one or more portions selected from among the leaves, the stalks and the flowers is preferable, and use of the leaves and/or the flowers is particularly desirable. Examples of the extraction solvent and the extraction method are the same as those described above for the extraction of edelweiss. Preferred extraction solvents include one or more solvents selected from among 1,3-butylene glycol aqueous solutions, 1,2-pentanediol aqueous solutions, propylene glycol aqueous solutions, ethanol aqueous solutions and water, and the use of a 1,3-butylene glycol aqueous solution is the most desirable.

The extract of creeping saxifrage (*Saxifraga sarmentosa*) is not particularly limited, provided the extract can be blended into the external skin preparation. The portion of the creeping saxifrage that is extracted is not particularly limited, and one or more portions selected from among the entire plant, the leaves, the stalks, the flowers, the seeds and the roots may be used. Use of the leaves is preferable. Examples of the extraction solvent and the extraction method are the same as those described above for the extraction of edelweiss. Preferred extraction solvents include one or more solvents selected from among 1,3-butylene glycol aqueous solutions, 1,2-pentanediol aqueous solutions, propylene glycol aqueous solutions, ethanol aqueous solutions and water, and the use of a 1,3-butylene glycol aqueous solution is the most desirable.

The extract of European elderberry (*Sambucus nigra*) is not particularly limited, provided the extract can be blended into the external skin preparation. The portion of the European elderberry that is extracted is not particularly limited, and one or more portions selected from among the entire plant, the leaves, the stalks, the flowers, the fruit and the roots may be used. Use of the leaves is preferable. Examples of the extraction solvent and the extraction method are the same as those described above for the extraction of edelweiss. Preferred extraction solvents include one or more solvents selected from among 1,3-butylene glycol aqueous solutions, 1,2-pentanediol aqueous solutions, propylene glycol aqueous solutions, ethanol aqueous solutions and water.

The amount of the one or more extracts selected from the group consisting of extracts of plants belonging to the genus *Artemisia*, pipsissewa extract, olive extract, jojoba extract, carambola extract, clove extract, chamomile extract, carrot extract, daisy extract, peach kernel extract, marsh mallow extract, cinnamon bark extract, told extract, marigold extract, parsley extract, coltsfoot extract, creeping saxifrage extract and European elderberry extract added to the external skin preparation as the extract (2) varies depending on the presence of solvent in the extract(s) and the extract(s) formulation, but is typically about 0.0001 to 1% by mass. The amount is more preferably from 0.001 to 1% by mass, and still more preferably from 0.01 to 1% by mass.

As mentioned above, the extract (2) is preferably obtained using one or more extraction solvents selected from the group consisting of 1,3-butylene glycol aqueous solutions, 1,2-pentanediol aqueous solutions, propylene glycol aqueous solutions, ethanol aqueous solutions and water.

In addition to the essential components described above, the external skin preparation of the present embodiment may also include, according to need, appropriate amounts of one or more of the water-based components, oil-based components, moisturizers, colorants, surfactants, ultraviolet absorbers, thickeners, cosmetic components, fragrances, polymeric substances, antibacterial and antifungal agents, alcohols, powders, scrubbing agents, and biologically derived components and the like typically used in external skin preparations.

The external skin preparation of the present embodiment can be used, for example, in the form of a lotion, an emulsion or an ointment. Further, there are no particular limitations on the method used for producing the external skin preparation of the present embodiment.

Specific examples of preferred embodiments include creams, milky lotions, skin lotions, beauty essences, water-based gels, cleansing materials, facial cleansing foams, makeup base creams, milky lotion-like foundations, water-in-oil emollient creams, packs, bath additives, and sheet-like packs, but this is not an exhaustive list.

As described above, by combining an edelweiss extract and a specific extract (2) described above, effects such as improved skin turnover, improved skin barrier function and improved antioxidant function are enhanced synergistically, and a superior moisturizing effect and anti-aging effect can be obtained.

EXAMPLES

The embodiments of the present invention are described below in further detail using a series of examples, but the scope of the invention is in no way limited by these examples. Unless specifically stated otherwise, amounts are listed as mass % values.

First is a description of preparation examples for the extracts of the various plants that were used.

[Edelweiss Extract]

The entire above-ground portion of the edelweiss plant was dried, chopped finely, and then immersed in a 50% by mass aqueous solution of ethanol having a mass 10 times that of the plant. Following filtering, the filtrate was collected, and the solvent was removed by distillation. The resulting extract was dissolved in an aqueous solution of glycerol and ethanol, left to age, and then filtered a second time to obtain an edelweiss extract. [*Artemisia montana* Extract]

Leaves of *Artemisia montana* were dried, chopped finely, and then immersed in a 50% by mass aqueous solution of ethanol having a mass 10 times that of the plant. Following filtering, the filtrate was collected, and the solvent was removed by distillation. The resulting extract was dissolved in a 50% by mass aqueous solution of 1,3-butylene glycol, left to age, and then filtered a second time to obtain an *Artemisia montana* extract.

[Pipsissewa Extract]

Pipsissewa leaves were dried, chopped finely, and then immersed in a 50% by mass aqueous solution of ethanol having a mass 10 times that of the plant. Following filtering, the filtrate was collected, and the solvent was removed by distillation. The resulting extract was dissolved in a 50% by mass aqueous solution of 1,3-butylene glycol, left to age, and then filtered a second time to obtain a pipsissewa extract.

[Olive Extract]

Olive leaves were dried, chopped finely, and then immersed in a 50% by mass aqueous solution of ethanol having a mass 10 times that of the plant. Following filtering, the filtrate was collected, and the solvent was removed by distillation. The resulting extract was dissolved in a 50% by mass aqueous solution of 1,3-butylene glycol, left to age, and then filtered a second time to obtain an olive extract.

[Jojoba Extract]

Jojoba leaves were dried, chopped finely, and then immersed in a 50% by mass aqueous solution of ethanol having a mass 10 times that of the plant. Following filtering, the filtrate was collected, and the solvent was removed by distillation. The resulting extract was dissolved in a 50% by mass aqueous solution of 1,3-butylene glycol, left to age, and then filtered a second time to obtain a jojoba extract.

[Carambola Extract]

Carambola leaves were dried, chopped finely, and then immersed in an 80% by mass aqueous solution of ethanol having a mass 10 times that of the plant. Following filtering, the filtrate was collected, and the solvent was removed by distillation. The resulting extract was dissolved in a 30% by mass aqueous solution of 1,3-butylene glycol, left to age, and then filtered a second time to obtain a carambola extract.

[Clove Extract]

Clove buds were dried, chopped finely, and then immersed in a 50% by mass aqueous solution of ethanol having a mass 10 times that of the plant. Following filtering, the filtrate was collected, and the solvent was removed by distillation. The resulting extract was dissolved in a 50% by mass aqueous solution of ethanol, left to age, and then filtered a second time to obtain a clove extract.

[Chamomile Extract]

Chamomile flowers were dried, chopped finely, and then immersed in a 50% by mass aqueous solution of 1,3-butylene glycol having a mass 10 times that of the plant. Following filtering, the filtrate was collected, and the solvent was removed by distillation. The resulting extract was dissolved in a 50% by mass aqueous solution of 1,3-butylene glycol, left to age, and then filtered a second time to obtain a chamomile extract.

[Carrot Extract]

Carrot roots were washed and ground into a paste, and following aging, the paste was immersed in a 20% by mass aqueous solution of 1,3-butylene glycol. Following filtering, the filtrate was collected, left to age a second time, and then filtered again to obtain a carrot extract.

[Daisy Extract]

Daisy flowers were dried, chopped finely, and then immersed in water. Following filtering, the filtrate was collected, and the solvent was removed by distillation. The resulting extract was dissolved in water, left to age, and then filtered a second time to obtain a daisy extract.

[Peach Kernel Extract]

Mountain peach kernels were dried, chopped finely, and then immersed in a 50% by mass aqueous solution of ethanol. Following filtering, the filtrate was collected, left to age in a cold place, and then filtered a second time to obtain a peach kernel extract.

[Marsh Mallow Extract]

Marsh mallow roots were dried, chopped finely, and then immersed in a 50% by mass aqueous solution of 1,3-butylene glycol. Following filtering, the filtrate was collected, left to age in a cold place, and then filtered a second time to obtain a marsh mallow extract.

[Cinnamon Bark Extract]

Dried cinnamon bark was chopped finely and immersed in water, and following filtering, the filtrate was collected, and the solvent was removed by distillation. The resulting extract was dissolved in a 25% by mass aqueous solution of ethanol, left to age, and then filtered a second time to obtain a cinnamon bark extract.

[Toki Extract]

Toki roots were dried, chopped finely, immersed in a 50% by mass aqueous solution of 1,3-butylene glycol, and then filtered to obtain a told extract.

[Marigold Extract]

Marigold flower heads were chopped finely, and then immersed in a 50% by mass aqueous solution of 1,3-butylene glycol. Following filtering, the filtrate was collected, left to age in a cold place, and then filtered a second time to obtain a marigold extract.

[Parsley Extract]

Parsley was chopped finely, immersed in water, and then filtered to obtain a parsley extract.

[Coltsfoot Extract]

Coltsfoot flowers were dried, chopped finely, immersed in a 50% by mass aqueous solution of 1,3-butylene glycol, and then filtered to obtain a coltsfoot extract.

[Creeping Saxifrage Extract]

Creeping saxifrage leaves were dried, chopped finely, immersed in a 50% by mass aqueous solution of 1,3-butylene glycol, and then filtered to obtain a creeping saxifrage extract.

[European Elderberry Extract]

European elderberry flowers were dried, chopped finely, immersed in a 50% by mass aqueous solution of 1,3-butylene glycol, and then filtered to obtain a European elderberry extract.

[Example 1] Cream

| | |
|---|---|
| (1) Squalane | 10.0 (mass %) |
| (2) Stearic acid | 2.0 |
| (3) Hydrogenated palm kernel oil | 0.5 |
| (4) Hydrogenated soybean phospholipid | 0.1 |
| (5) Cetanol | 3.6 |
| (6) Lipophilic glycerol monostearate | 2.0 |
| (7) Glycerol | 10.0 |
| (8) Methyl para-oxybenzoate | 0.1 |
| (9) Arginine (20% by mass aqueous solution) | 15.0 |
| (10) Purified water | amount required to make total amount up to 100 |
| (11) Carboxyvinyl polymer (1% by mass aqueous solution) | 15.0 |
| (12) Edelweiss extract | 0.5 |
| (13) Extract shown in Table 1A | 0.5 |

Preparation Method:

The oil phase components (1) to (6) were heated and dissolved at 80° C. In a separate preparation, the water phase components (7) to (10) were also heated and dissolved at 80° C. The oil phase components were then added to the water phase components under constant stirring, and the resulting mixture was emulsified uniformly using a homogenizer. Following completion of the emulsification, the component (11) was added, cooling was started, and when the temperature reached 40° C., the components (12) and (13) were added and mixed uniformly.

[Comparative Example 1] Cream

| | |
|---|---|
| (1) Squalane | 10.0 (mass %) |
| (2) Stearic acid | 2.0 |
| (3) Hydrogenated palm kernel oil | 0.5 |
| (4) Hydrogenated soybean phospholipid | 0.1 |
| (5) Cetanol | 3.6 |
| (6) Lipophilic glycerol monostearate | 2.0 |
| (7) Glycerol | 10.0 |
| (8) Methyl para-oxybenzoate | 0.1 |
| (9) Arginine (20% by mass aqueous solution) | 15.0 |
| (10) Purified water | amount required to make total amount up to 100 |
| (11) Carboxyvinyl polymer (1% by mass aqueous solution) | 15.0 |
| (12) Extract shown in Table 1A | 1.0 |

Preparation Method:

The oil phase components (1) to (6) were heated and dissolved at 80° C. In a separate preparation, the water phase components (7) to (10) were also heated and dissolved at 80° C. The oil phase components were then added to the water phase components under constant stirring, and the resulting mixture was emulsified uniformly using a homogenizer. Following completion of the emulsification, the component (11) was added, cooling was started, and when the temperature reached 40° C., the component (12) was added and mixed uniformly.

(Evaluation of Moisturizing Properties)

A single group composed of 15 male and female panelists used each of the creams of Example 1 (1-1 to 1-18) shown in Table 1A simultaneously with the corresponding cream of Comparative Example 1 (1-1 to 1-8) in a blind test, and after 30 minutes, each panelist was asked to select the cream which he/she felt yielded a superior moisturizing effect. A score of "+1" was recorded if the Example yielded a superior moisturizing effect to the Comparative Example, a score of "0" was recorded if the two creams were about the same, and a score of "−1" was recorded if the Comparative Example yielded a superior moisturizing effect to the Example. The sum of all the scores was calculated, and a sum of 15 to 8 points was evaluated as "A", a sum of 7 to 0 points was evaluated as "B", and a sum of −1 or less was evaluated as "C". The results are shown in Table 1A.

TABLE 1A (Example 1, Comparative Example 1)

| Example | Plant extract used in combination with edelweiss extract | Comparative Example | Plant extract used alone | Moisturizing effect |
|---|---|---|---|---|
| 1-1 | Artemisia extract | 1-1 | Artemisia extract | A |
| 1-2 | Pipsissewa extract | 1-2 | Pipsissewa extract | A |
| 1-3 | Olive extract | 1-3 | Olive extract | A |
| 1-4 | Jojoba extract | 1-4 | Jojoba extract | A |
| 1-5 | Carambola extract | 1-5 | Carambola extract | A |
| 1-6 | Clove extract | 1-6 | Clove extract | A |
| 1-7 | Chamomile extract | 1-7 | Chamomile extract | A |
| 1-8 | Carrot extract | 1-8 | Carrot extract | A |
| 1-9 | Daisy extract | 1-9 | Daisy extract | A |
| 1-10 | Peach kernel extract | 1-10 | Peach kernel extract | A |
| 1-11 | Marsh mallow extract | 1-11 | Marsh mallow extract | A |
| 1-12 | Cinnamon bark extract | 1-12 | Cinnamon bark extract | A |
| 1-13 | Toki extract | 1-13 | Toki extract | A |
| 1-14 | Marigold extract | 1-14 | Marigold extract | A |
| 1-15 | Parsley extract | 1-15 | Parsley extract | A |
| 1-16 | Coltsfoot extract | 1-16 | Coltsfoot extract | A |
| 1-17 | Creeping saxifrage extract | 1-17 | Creeping saxifrage extract | A |
| 1-18 | European elderberry extract | 1-18 | European elderberry extract | A |

As a result of including a combination of the edelweiss extract and a specific plant extract, the cream of each Example exhibited an extremely superior moisturizing effect compared with the cream of the corresponding Comparative Example which contained only the specific plant extract.

Moreover, the change in the corneous moisture content (skin moisture content) was measured for the Example 1 group and the Comparative Example 1 group described above, and also for an external skin preparations containing only the edelweiss extract (Comparative Example A) and an external skin preparations containing absolutely no plant extracts (Comparative Example B).

(Measurement of Corneous Moisture Content)

The test method used was as follows.

The inner portions of the forearms were scrubbed ten times with a foamed facial cleansing material, and following rinsing for 10 seconds with lukewarm water, moisture was wiped off the forearms, and the forearms were held still for 30 minutes in an environment of 20° C. and a relative humidity of 50%.

Three regions of 2.5 cm×2.5 cm were marked on each of the left and right forearms, and the corneous moisture content of each region was measured prior to application of the skin preparation. Subsequently, the external skin preparation of the Example or Comparative Example shown in Table 1B was applied, and 30 minutes after the application, the corneous moisture content was remeasured.

The testers were instructed not to use any cosmetic materials on the inner forearms for 1 week prior to the test, and when performing the test, each measurement region was used only once.

Application of the sample preparation was performed as follows. A spatula was placed on a precision electronic balance, 10 mg of the sample was weighed onto the spatula, and the spatula was then used to apply the external skin preparation to one of the 2.5 cm×2.5 cm regions.

The corneous moisture content was measured using a SKICON-200 apparatus manufactured by IBS Co., Ltd., by performing 5 measurements within each region, and recording the average value as the corneous moisture content. The corneous moisture content 30 minutes after application was calculated as a relative value, relative to an corneous moisture content prior to application of 1. The results are shown in Table 1B.

As illustrated in Table 1B, in the Comparative Example 1 group and Comparative Example A, which used an external skin preparation containing one of the specific plant extracts or the edelweiss extract as a lone extract, an increase in the corneous moisture content was observed compared with the Comparative Example B which contained absolutely no extracts. However, the increase in the corneous moisture content in the group using the external skin preparations of Example 1 yielded superior values that were at least twice that of the Comparative Examples.

In other words, despite the fact that the total amount of plant extract(s) added was 1% by mass in both the Examples and the Comparative Examples, a dramatic improvement in the corneous moisture content was observed for the external skin preparations of the Examples, confirming that using a combination of the edelweiss extract and a specific plant extract yielded a synergistic improvement in the moisturizing effect.

[Example 2] Milky Lotion

| | |
|---|---|
| (1) Squalane | 10.0 (mass %) |
| (2) Methylphenylpolysiloxane | 4.0 |
| (3) Hydrogenated palm kernel oil | 0.5 |
| (4) Hydrogenated soybean phospholipid | 0.1 |
| (5) Polyoxyethylene (20 E.O.) sorbitan monostearate | 1.3 |
| (6) Sorbitan monostearate | 1.0 |
| (7) Glycerol | 4.0 |
| (8) Methyl para-oxybenzoate | 0.1 |
| (9) Carboxyvinyl polymer | 0.15 |
| (10) Purified water | amount required to make total amount up to 100 |
| (11) Arginine (1% by mass aqueous solution) | 20.0 |
| (12) Edelweiss extract | 0.3 |
| (13) Extract shown in Table 2 | 0.3 |

Preparation Method:

The oil phase components (1) to (6) were heated and dissolved at 80° C. In a separate preparation, the water phase components (7) to (10) were also heated and dissolved at 80° C. The oil phase components were then added to the water phase components under constant stirring, and the resulting mixture was emulsified uniformly using a homogenizer.

TABLE 1B (Example 1, Comparative Example 1)

| Example | Plant extract used in combination with edelweiss extract | Moisture content | Comparative Example | Plant extract used alone | Moisture content |
|---|---|---|---|---|---|
| 1-1 | Artemisia extract | 6.84 | 1-1 | Artemisia extract | 3.27 |
| 1-2 | Pipsissewa extract | 8.45 | 1-2 | Pipsissewa extract | 3.55 |
| 1-5 | Carambola extract | 7.69 | 1-5 | Carambola extract | 3.68 |
| 1-6 | Clove extract | 7.14 | 1-6 | Clove extract | 3.42 |
| 1-8 | Carrot extract | 6.95 | 1-8 | Carrot extract | 3.45 |
| 1-9 | Daisy extract | 8.27 | 1-9 | Daisy extract | 3.67 |
| 1-10 | Peach kernel extract | 7.84 | 1-10 | Peach kernel extract | 3.42 |
| 1-11 | Marsh mallow extract | 7.59 | 1-11 | Marsh mallow extract | 3.54 |
| 1-12 | Cinnamon bark extract | 7.51 | 1-12 | Cinnamon bark extract | 3.59 |
| 1-14 | Marigold extract | 6.99 | 1-14 | Marigold extract | 3.46 |
| 1-15 | Parsley extract | 6.71 | 1-15 | Parsley extract | 3.71 |
| 1-16 | Coltsfoot extract | 7.45 | 1-16 | Coltsfoot extract | 3.49 |
| 1-17 | Creeping saxifrage extract | 8.26 | 1-17 | Creeping saxifrage extract | 3.61 |
| | | | Comparative Example A | Edelweiss extract | 3.26 |
| | | | Comparative Example B | No extracts | 2.64 |

Following completion of the emulsification, cooling was started, and the components (11) to (13) were added sequentially and mixed uniformly.

TABLE 2

(Example 2)

| Example | Plant extract used in combination with edelweiss extract |
|---|---|
| 2-1 | *Artemisia* extract |
| 2-2 | Pipsissewa extract |
| 2-3 | Olive extract |
| 2-4 | Jojoba extract |
| 2-5 | Carambola extract |
| 2-6 | Clove extract |
| 2-7 | Chamomile extract |
| 2-8 | Carrot extract |
| 2-9 | Daisy extract |
| 2-10 | Peach kernel extract |
| 2-11 | Marsh mallow extract |
| 2-12 | Cinnamon bark extract |
| 2-13 | Toki extract |
| 2-14 | Marigold extract |
| 2-15 | Parsley extract |
| 2-16 | Coltsfoot extract |
| 2-17 | Creeping saxifrage extract |
| 2-18 | European elderberry extract |

[Example 3] Skin Lotion

| | |
|---|---|
| (1) Ethanol | 15.0 (mass %) |
| (2) Polyoxyethylene (40 E.O.) hydrogenated castor oil | 0.3 |
| (3) Fragrance | 0.1 |
| (4) Purified water | amount required to make total amount up to 100 |
| (5) Citric acid | 0.02 |
| (6) Sodium citrate | 0.1 |
| (7) Glycerol | 1.0 |
| (8) Hydroxyethyl cellulose | 0.1 |
| (9) Edelweiss extract | 0.3 |
| (10) Extract shown in Table 2 | 0.3 |

Preparation Method:

The components (2) and (3) were dissolved in the component (1). Following dissolution, the components (4) to (8) were added sequentially, and following thorough stirring, the components (9) and (10) were added and mixed uniformly.

[Example 4] Beauty Essence

| | |
|---|---|
| (1) Purified water | amount required to make total amount up to 100 |
| (2) Glycerol | 10.0 (mass %) |
| (3) Sucrose fatty acid ester | 1.3 |
| (4) Carboxyvinyl polymer (1% by mass aqueous solution) | 17.5 |
| (5) Sodium alginate (1% by mass aqueous solution) | 15.0 |
| (6) Polyglyceryl monolaurate | 1.0 |
| (7) Macadamia nut oil fatty acid phytosteryl | 3.0 |
| (8) Di(phytosteryl-2-octyldodecyl) N-lauroyl-L-glutamate | 2.0 |
| (9) Hydrogenated palm oil | 2.0 |
| (10) Squalane (derived from olive) | 1.0 |
| (11) Behenyl alcohol | 0.75 |
| (12) Beeswax | 1.0 |
| (13) Jojoba oil | 1.0 |
| (14) 1,3-butylene glycol | 10.0 |
| (15) L-arginine (10% by mass aqueous solution) | 2.0 |
| (16) Edelweiss extract | 0.2 |
| (17) Peach kernel extract | 0.2 |
| (18) Pipsissewa extract | 0.2 |
| (19) *Artemisia* extract | 0.2 |
| (20) Jojoba extract | 0.2 |

Preparation Method:

The water phase components (1) to (6) were mixed, and then heated and dissolved at 75° C. In a separate preparation, the oil phase components (7) to (14) were also heated and dissolved at 75° C. The oil phase components were then added to the water phase components, and following preliminary emulsification, the mixture was emulsified uniformly using a homomixer. Following completion of the emulsification, cooling was started, and the component (15) was added at a temperature of 50° C. Cooling was then continued to 40° C., and the components (16) to (20) were added and mixed uniformly.

[Example 5] Water-Based Gel

| | |
|---|---|
| (1) Carboxyvinyl polymer | 0.5 (mass %) |
| (2) Purified water | amount required to make total amount up to 100 |
| (3) Sodium hydroxide (10% by mass aqueous solution) | 0.5 |
| (4) Methyl para-oxybenzoate | 0.1 |
| (5) Edelweiss extract | 0.3 |
| (6) Peach kernel extract | 0.3 |
| (7) Ethanol | 10.0 |
| (8) Fragrance | 0.1 |
| (9) Polyoxyethylene (60 E.O.) hydrogenated castor oil | 0.1 |

Preparation Method:

The component (1) was added to the component (2), and following uniform stirring, the component (3) was added. After stirring to obtain a uniform mixture, the components (4) to (9) were added and mixed uniformly.

[Example 6] Cleansing Material

| | |
|---|---|
| (1) Squalane | 81.0 (mass %) |
| (2) Polyoxyethylene glyceryl isostearate | 15.0 |
| (3) Purified water | amount required to make total amount up to 100 |
| (4) Edelweiss extract | 0.5 |
| (5) Pipsissewa extract | 0.5 |

Preparation Method:

The components (1) and (2) were dissolved uniformly. The components (3) to (5) were then added sequentially and mixed uniformly.

[Example 7] Facial Cleansing Foam

| | |
|---|---|
| (1) Stearic acid | 16.0 (mass %) |
| (2) Myristic acid | 16.0 |

|     |     |
| --- | --- |
| (3) Lipophilic glycerol monostearate | 2.0 |
| (4) Glycerol | 20.0 |
| (5) Sodium hydroxide | 7.5 |
| (6) Coconut oil fatty acid amidopropyl betaine | 1.0 |
| (7) Purified water | amount required to make total amount up to 100 |
| (8) Edelweiss extract | 0.4 |
| (9) *Artemisia* extract | 0.4 |

Preparation Method:

The oil phase components (1) to (4) were heated and dissolved at 80° C. The water phase components (5) to (7) were also heated and dissolved at 80° C., and were then mixed uniformly with the oil phase components. Cooling was started, and the components (8) and (9) were added at a temperature of 40° C. and mixed uniformly.

[Example 8] Makeup Base Cream

|     |     |
| --- | --- |
| (1) Squalane | 10.0 (mass %) |
| (2) Cetanol | 2.0 |
| (3) Glycerol tri-2-ethylhexanoate | 2.5 |
| (4) Lipophilic glyceryl monostearate | 1.0 |
| (5) Propylene glycol | 11.0 |
| (6) Sucrose fatty acid ester | 1.3 |
| (7) Purified water | amount required to make total amount up to 100 |
| (8) Titanium oxide | 1.0 |
| (9) Red iron oxide | 0.1 |
| (10) Yellow iron oxide | 0.4 |
| (11) Fragrance | 0.1 |
| (12) Edelweiss extract | 0.2 |
| (13) Jojoba extract | 0.1 |
| (14) Carambola extract | 0.1 |

Preparation Method:

The oil phase components (1) to (4) were mixed, and then heated and dissolved at 75° C. In a separate preparation, the water phase components (5) to (7) were also mixed, and heated and dissolved at 75° C., and the pigments of components (8) to (10) were then added and dispersed uniformly using a homomixer. The oil phase components were then added to the water phase components, and the resulting mixture was emulsified using a homomixer. Following completion of the emulsification, cooling was started, and the components (11) to (14) were added at a temperature of 40° C. and mixed uniformly.

[Example 9] Milky Lotion-Like Foundation

|     |     |
| --- | --- |
| (1) Methylpolysiloxane | 2.0 (mass %) |
| (2) Squalane | 5.0 |
| (3) Octyldodecyl myristate | 5.0 |
| (4) Cetanol | 1.0 |
| (5) Polyoxyethylene (20 E.O.) sorbitan monostearate | 1.3 |
| (6) Sorbitan monostearate | 0.7 |
| (7) 1,3-butylene glycol | 8.0 |
| (8) Xanthan gum | 0.1 |
| (9) Methyl para-oxybenzoate | 0.1 |
| (10) Purified water | amount required to make total amount up to 100 |
| (11) Titanium oxide | 9.0 |
| (12) Talc | 7.4 |
| (13) Red iron oxide | 0.5 |
| (14) Yellow iron oxide | 1.1 |
| (15) Black iron oxide | 0.1 |
| (16) Fragrance | 0.1 |
| (17) Edelweiss extract | 0.2 |
| (18) *Artemisia* extract | 0.1 |
| (19) Olive extract | 0.1 |

Preparation Method:

The oil phase components (1) to (6) were mixed, and then heated and dissolved at 75° C. In a separate preparation, the water phase components (7) to (10) were also mixed, and heated and dissolved at 75° C., and the pigments of components (11) to (15) were then added and dispersed uniformly using a homomixer. The oil phase components were then added to the water phase components, and the resulting mixture was emulsified. Following completion of the emulsification, cooling was started, and the components (16) to (19) were added sequentially at a temperature of 40° C. and mixed uniformly.

[Example 10] Water-in-Oil Emollient Cream

|     |     |
| --- | --- |
| (1) Liquid paraffin | 30.0 (mass %) |
| (2) Microcrystalline wax | 2.0 |
| (3) Vaseline | 5.0 |
| (4) Diglycerol oleate | 5.0 |
| (5) Sodium chloride | 1.3 |
| (6) Potassium chloride | 0.1 |
| (7) Propylene glycol | 3.0 |
| (8) 1,3-butylene glycol | 5.0 |
| (9) Methyl para-oxybenzoate | 0.1 |
| (10) Edelweiss extract | 0.2 |
| (11) Clove extract | 0.1 |
| (12) *Artemisia* extract | 0.1 |
| (13) Purified water | amount required to make total amount up to 100 |
| (14) Fragrance | 0.1 |

Preparation Method:

The components (5) and (6) were dissolved in a portion of the component (13), and the solution was heated to 50° C. and then added gradually with constant stirring to the component (4) which had also been heated to 50° C. Following mixing, the mixture was dispersed uniformly in a solution of the components (1) to (3) which had been dissolved by heating at 70° C. Another solution prepared by heating and dissolving the components (7) to (12) in the remainder of the component (13) at 70° C. was then added to the uniform dispersion under constant stirring, and the resulting mixture was emulsified using a homomixer. Following completion of the emulsification, cooling was started, and the component (14) was added at a temperature of 40° C. and mixed uniformly.

[Example 11] Pack

|     |     |
| --- | --- |
| (1) Purified water | amount required to make total amount up to 100 |
| (2) Polyvinyl alcohol | 12.0 (mass %) |
| (3) Ethanol | 17.0 |

-continued

|  |  |
|---|---|
| (4) Glycerol | 5.0 |
| (5) Polyethylene glycol (average molecular weight: 1,000) | 2.0 |
| (6) Edelweiss extract | 0.2 |
| (7) Jojoba extract | 0.2 |
| (8) Marigold extract | 0.2 |
| (9) Chamomile extract | 0.2 |
| (10) Fragrance | 0.1 |

Preparation Method:

The components (2) and (3) were mixed, and following heating to 80° C., the mixture was dissolved in the component (1) which had also been heated to 80° C. Following uniform dissolution, the components (4) and (5) were added, and cooling was started under constant stirring. The solution was cooled to 40° C., and the components (6) to (10) were then added and mixed uniformly.

[Example 12] Bath Additive

|  |  |
|---|---|
| (1) Fragrance | 0.3 (mass %) |
| (2) Edelweiss extract | 0.2 |
| (3) Marsh mallow extract | 0.2 |
| (4) Sodium bicarbonate | 50.0 |
| (5) Sodium sulfate | 49.3 |

Preparation Method:

The components (1) to (5) were mixed together uniformly.

[Example 13] Sheet-Like Pack

|  |  |
|---|---|
| (1) Fragrance | 0.1 (mass %) |
| (2) 1,3-butylene glycol | 5.0 |
| (3) Glycerol | 5.0 |
| (4) Ethanol | 3.0 |
| (5) Edelweiss extract | 0.2 |
| (6) Creeping saxifrage extract | 0.2 |
| (7) Purified water | amount required to make total amount up to 100 |

Preparation Method:

The components (1) to (7) were mixed together uniformly, and the mixture was then impregnated into a nonwoven sheet.

(Confirmation of Synergistic Effect)

The procedure described below was used to confirm that combining the edelweiss extract and a specific plant extract in an external skin preparation yielded synergistic enhancements in effects such as improved skin turnover, improved skin barrier function and improved antioxidant function.

Human epidermal keratinocytes were inoculated in a 6-well plate in an amount of $3\times10^5$ cells/well, and were cultured overnight in a DMEM medium containing 5% FBS. The medium was then replaced with a medium containing a dissolved plant extract, and culturing was performed for 24 hours at 37° C. in a 5% $CO_2$ incubator. Total RNA extraction from the cells was performed using Trizol reagent in accordance with the protocol of Life Technologies Inc. Following cDNA synthesis, gene expression was confirmed by real-time PCR using the primers shown in the table below. The GAPDH shown in Table 3 below was used as an internal standard. Further, in the case of addition of a lone plant extract to the medium, the amount of the plant extract added was set to a concentration which exhibited no cell toxicity, whereas in the case of addition of a combination of extracts, the amount of each extract was set to half the amount added in the case where the extract was added as a lone extract.

TABLE 3

| EGFR | Forward: CCGTTTGGGAGTTGATGACC (SEQ ID NO: 1) Reverse: ATATGGGTGGCTGAGGGAGG (SEQ ID NO: 2) |
|---|---|
| KRT1 | Forward: GGATCATCAACTACCAGCGC (SEQ ID NO: 3) Reverse: TCCGACTTCCAAATCCACC (SEQ ID NO: 4) |
| KRT10 | Forward: AGCACTACTCTTCCTCCCGC (SEQ ID NO: 5) Reverse: GGCTAAAAGAGCCACCACTG (SEQ ID NO: 6) |
| KLK8 | Forward: TCCAAAGTGAAGCCCATCAG (SEQ ID NO: 7) Reverse: TGCACAGTTGAGAGTGTCAGG (SEQ ID NO: 8) |
| ABCA12 | Forward: GGCTGCACAGCTCCTAATTC (SEQ ID NO: 9) Reverse: GTGAACCTCTGGCCAAACTG (SEQ ID NO: 10) |
| CD44 | Forward: AACCATTACAGGGAGCTGGGACACTTAA (SEQ ID NO: 11) Reverse: TTTGTTAGAAGCCATCCATAGCACACCC (SEQ ID NO: 12) |
| IVL | Forward: CCTCAAGACTGTTCCTCCTCC (SEQ ID NO: 13) Reverse: CCCTTTACAGCAGTCATGTGC (SEQ ID NO: 14) |
| TGM1 | Forward: TACGTGGACCATGAGGATTG (SEQ ID NO: 15) Reverse: GCCGGTCCAGGATGTATAAG (SEQ ID NO: 16) |
| CLDN1 | Forward: GAAGACGATGAGGTGCAGAAG (SEQ ID NO: 17) Reverse: CCAGTGAAGAGAGCCTGACC (SEQ ID NO: 18) |
| SOD2 | Forward: TGCATCTGTTGGTGTCCAAG (SEQ ID NO: 19) Reverse: GTTCCTTGCAGTGGATCCTG (SEQ ID NO: 20) |
| GAPDH | Forward: CCACTCCTCCACCTTTGACG (SEQ ID NO: 21) Reverse: CACCCTGTTGCTGTAGCCAA (SEQ ID NO: 22) |

In FIG. 1 to FIG. 14, the vertical axis indicates a multiplication factor when the amount of RNA detected for each gene using the control was deemed to be 1.

As illustrated in FIG. 1 to FIG. 14, in the external skin preparations of the present embodiments, by combining the edelweiss extract and one of the specific plant extracts, effects such as improved skin turnover, improved skin barrier function and improved antioxidant function were enhanced synergistically, and a superior moisturizing effect and anti-aging effect were obtained.

It is to be noted that, besides those already mentioned above, many modifications and variations of the above embodiments may be made without departing from the novel and advantageous features of the present invention. Accordingly, all such modifications and variations are intended to be included within the scope of the appended claims.

The invention claimed is:

1. A moisturizing external skin preparation comprising a synergistically effective amount of the combination of an edelweiss extract and one or more additional extracts selected from pipsissewa extract, carambola extract, and parsley extract.

2. The moisturizing external skin preparation according to claim 1, wherein the edelweiss extract includes at least one selected from an extract of an entire plant, an extract of a stalk, an extract of a flower, an extract of a leaf, and an extract of a root.

3. The moisturizing external skin preparation according to claim 1, wherein the edelweiss extract includes an extract of an entire plant except root.

4. The moisturizing external skin preparation according to claim 1, wherein the pipsissewa extract includes at least one selected from an extract of an entire plant, an extract of a stalk, an extract of a flower, and an extract of a leaf.

5. The moisturizing external skin preparation according to claim 1, wherein the pipsissewa extract includes an extract of an entire plant.

6. The moisturizing external skin preparation according to claim 1, wherein the carambola extract includes at least one selected from an extract of a leaf, an extract of a flower, and an extract of a fruit.

7. The moisturizing external skin preparation according to claim 1, wherein the carambola extract includes an extract of a leaf.

8. The moisturizing external skin preparation according to claim 1, wherein the parsley extract includes at least one selected from an extract of an entire plant, an extract of a leaf, an extract of a stalk, an extract of a flower, an extract of a seed, and an extract of a root.

9. The moisturizing external skin preparation according to claim 1, wherein the parsley extract includes at least one selected from an extract of a leaf and an extract of a stalk.

10. The moisturizing external skin preparation according to claim 1, wherein the edelweiss extract includes at least one selected from an extract of an entire plant, an extract of a stalk, an extract of a flower, an extract of a leaf, and an extract of a root;

the pipsissewa extract includes at least one selected from an extract of an entire plant, an extract of a stalk, an extract of a flower, and an extract of a leaf;

the carambola extract includes at least one selected from an extract of a leaf, an extract of a flower, and an extract of a fruit; and the parsley extract includes at least one selected from an extract of an entire plant, an extract of a leaf, an extract of a stalk, an extract of a flower, an extract of a seed, and an extract of a root.

11. The moisturizing external skin preparation according to claim 1, wherein the edelweiss extract includes an extract of an entire plant except root;

the pipsissewa extract includes an extract of an entire plant;

the carambola extract includes an extract of a leaf; and the parsley extract includes at least one of an extract of a leaf and an extract of a stalk.

12. The moisturizing external skin preparation according to claim 1, wherein an extraction solvent for the edelweiss extract, the pipsissewa extract, the carambola extract, and the parsley extract includes at least one of water and ethanol.

* * * * *

SEQUENCE LISTING

<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccgtttggga gttgatgacc                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atatgggtgg ctgagggagg                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggatcatcaa ctaccagcgc                                              20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tccgacttcc aaatccacc                                               19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agcactactc ttcctcccgc                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggctaaaaga gccaccactg                                              20

```
<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tccaaagtga agcccatcag                                                 20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgcacagttg agagtgtcag g                                               21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggctgcacag ctcctaattc                                                 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtgaacctct ggccaaactg                                                 20

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaccattaca gggagctggg acacttaa                                        28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttgttagaa gccatccata gcacaccc                                        28
```

```
<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cctcaagact gttcctcctc c                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccctttacag cagtcatgtg c                                              21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tacgtggacc atgaggattg                                                20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gccggtccag gatgtataag                                                20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaagacgatg aggtgcagaa g                                              21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccagtgaaga gagcctgacc                                                20
```

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgcatctgtt ggtgtccaag                                                     20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gttccttgca gtggatcctg                                                     20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccactcctcc acctttgacg                                                     20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caccctgttg ctgtagccaa                                                     20
```